US012594379B2

(12) United States Patent
Pirbodaghi et al.

(10) Patent No.: US 12,594,379 B2
(45) Date of Patent: Apr. 7, 2026

(54) BACKFLOW PREVENTION MECHANISM FOR DRUG DELIVERY DEVICE

(71) Applicant: AMGEN INC., Thousand Oaks, CA (US)

(72) Inventors: Tohid Pirbodaghi, Cambridge, MA (US); Paul Daniel Faucher, Escondido, CA (US); Joshua Tamsky, Los Angeles, CA (US); Scott Robert Gibson, Simi Valley, CA (US); Sheldon B. Moberg, Thousand Oaks, CA (US); Jeff Lind, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1057 days.

(21) Appl. No.: 17/637,507

(22) PCT Filed: Sep. 9, 2020

(86) PCT No.: PCT/US2020/049864
§ 371 (c)(1),
(2) Date: Feb. 23, 2022

(87) PCT Pub. No.: WO2021/050494
PCT Pub. Date: Mar. 18, 2021

(65) Prior Publication Data
US 2022/0362462 A1      Nov. 17, 2022

Related U.S. Application Data

(60) Provisional application No. 62/899,525, filed on Sep. 12, 2019, provisional application No. 62/899,538, filed on Sep. 12, 2019.

(51) Int. Cl.
*A61M 5/168*        (2006.01)
*A61M 5/158*        (2006.01)
(Continued)

(52) U.S. Cl.
CPC ........ *A61M 5/16813* (2013.01); *A61M 5/158* (2013.01); *A61M 5/3287* (2013.01);
(Continued)

(58) Field of Classification Search
CPC .............. A61M 5/16813; A61M 5/158; A61M 5/3287; A61M 2005/1585;
(Continued)

(56) References Cited

U.S. PATENT DOCUMENTS

| | | | |
|---|---|---|---|
| 4,804,015 A * | 2/1989 | Albinsson | ............. A61M 39/26 |
| | | | 251/342 |
| 5,527,307 A | 6/1996 | Srisathapat et al. | |

(Continued)

FOREIGN PATENT DOCUMENTS

| | | |
|---|---|---|
| EP | 1980290 A1 | 10/2008 |
| EP | 1993633 B1 | 11/2016 |

(Continued)

OTHER PUBLICATIONS

International Search Report and Written Opinion of International Application No. PCT/US2020/049864, dated Dec. 18, 2020.

(Continued)

*Primary Examiner* — Theodore J Stigell
(74) *Attorney, Agent, or Firm* — MARSHALL, GERSTEIN & BORUN LLP

(57)        ABSTRACT

A drug delivery device includes a housing, a container disposed in the housing, an activation mechanism, a needle insertion mechanism, a fluid flow connection, and a valve in fluid communication with the fluid flow connection and the needle insertion mechanism. The container has an inner volume to contain a medicament which is urged out of the container by the activation mechanism. The needle insertion mechanism is adapted to insert a needle and/or a cannula to deliver the medicament from the container via the fluid flow (Continued)

connection. The valve is in fluid communication with the fluid flow connection and needle insertion mechanism, and is movable between first and second positions. Upon insertion of the needle and/or the cannula, the valve remains in the first position whereby fluid flow is restricted. At a later time, the valve is urged to the second position whereby fluid may flow through the needle or cannula.

5 Claims, 8 Drawing Sheets

(51) Int. Cl.
*A61M 5/31* (2006.01)
*A61M 5/32* (2006.01)
(52) U.S. Cl.
CPC ............... *A61M 2005/1585* (2013.01); *A61M 2005/3128* (2013.01)
(58) Field of Classification Search
CPC .. A61M 2005/3128; A61M 2005/1406; A61M 5/1582; A61M 39/26; A61M 5/16881; A61M 2005/14252; A61M 5/14248
See application file for complete search history.

(56) References Cited

U.S. PATENT DOCUMENTS

| | | | |
|---|---|---|---|
| 9,511,189 B2 | 12/2016 | O'Connor et al. | |
| 2006/0122536 A1 | 6/2006 | Haar et al. | |
| 2012/0330235 A1 * | 12/2012 | Moga .................... | A61M 5/148 604/131 |
| 2013/0060233 A1 * | 3/2013 | O'Connor ......... | A61M 5/14248 604/151 |
| 2017/0224915 A1 | 8/2017 | Destefano et al. | |
| 2019/0151568 A1 | 5/2019 | Cardinali et al. | |

FOREIGN PATENT DOCUMENTS

| | | | |
|---|---|---|---|
| WO | WO-2018034784 A1 * | 2/2018 | |
| WO | WO-2019070472 A1 | 4/2019 | |

OTHER PUBLICATIONS

European Patent Application No. 20780440.2, Communication Pursuant to Article 94(3) EPC, dated Aug. 28, 2024.

\* cited by examiner

BACKFLOW PREVENTION MECHANISM FOR DRUG DELIVERY DEVICE

CROSS-REFERENCE TO RELATED APPLICATION

This is the United States national phase of International Patent Application No. PCT/US20/49864, filed Sep. 9, 2020, claiming priority to U.S. Application No. 62/899,525, filed Sep. 12, 2019, and U.S. Application No. 62/899,538, filed Sep. 12, 2019. The priority applications are hereby incorporated by reference in their entirety.

FIELD OF DISCLOSURE

The present disclosure generally relates to drug delivery devices and, more particularly, to drug delivery devices having backflow prevention mechanisms to assist in drug flow.

BACKGROUND

Drug delivery devices, such as injectors, are used to deliver liquid drugs to a patient. Upon activation, a drug delivery device may expel a drug stored within an internal reservoir of a primary container through a needle, cannula, or other delivery member into the patient. Some drug delivery devices may be temporarily attached to a patient to deliver a drug via an injection needle or some other means over an extended period of time. The drug delivery device may be releasably attached to the tissue of the patient's abdomen, thigh, arm, or some other portion of the patient's body.

Occlusions of the fluid path may occur, and clots may form within the fluid path of the drug delivery device. The coagulated material may prevent the drug from being delivered when the pressure required to push the drug through the clot (or to alternatively displace the clot) exceeds the drive force capability of the drug delivery device. Accordingly, the drug delivery device may stall, which can adversely impact delivery of the drug to the user, particularly with respect to delayed delivery devices. Delayed delivery devices may enhance the therapeutic efficacy of certain drugs while reducing or preventing adverse side effects. Such devices may be activated by a healthcare professional, thereby causing a needle and/or a cannula to be inserted into a patient's tissue, but may not administer the drug until after a predetermined delay.

As described in more detail below, the present disclosure sets forth systems for delivery devices embodying advantageous alternatives to existing systems and methods, and that may address one or more of the challenges or needs mentioned herein, as well as provide other benefits and advantages.

SUMMARY

In accordance with a first aspect, a drug delivery device includes a housing, a container disposed in the housing, an activation mechanism, a needle insertion mechanism, a fluid flow connection, and a valve in fluid communication with the fluid flow connection and the needle insertion mechanism. The container has an inner volume to contain a medicament which is urged out of the container by the activation mechanism. The needle insertion mechanism is adapted to insert a needle and/or a cannula to deliver the medicament from the container via the fluid flow connection. The valve is in fluid communication with the fluid flow connection and needle insertion mechanism, and is movable between first and second positions. Upon insertion of the needle and/or the cannula, the valve remains in the first position whereby fluid flow is restricted. At a later time, the valve is urged to the second position whereby fluid may flow through the needle or cannula.

In some approaches, the valve includes a valve pin septum and a valve pin. The valve pin septum includes a first throughbore and a second throughbore. The first throughbore accommodates the fluid flow connection to allow the medicament to flow therethrough. The valve pin is movably disposed within the second throughbore. In these examples, when the valve is in the first position, the valve pin is positioned within the first throughbore to restrict the medicament from flowing therethrough. Further, when the valve is in the second position, the valve pin is positioned to permit the medicament to flow through the first throughbore. The activation mechanism may be operably coupled with the valve pin to move the valve pin between the first and second positions.

In some examples, the needle insertion mechanism further includes a needle yoke and a cannula yoke. The needle yoke is operably coupled with the activation mechanism and includes a needle coupling portion to receive a portion of the needle. The cannula yoke is also operably coupled with the activation mechanism and includes a cannula coupling portion to receive a portion of the cannula, a fluid flow connection coupling portion to receive a portion of the fluid flow connection, and a valve coupling portion to receive a portion of the valve. In these examples, the activation mechanism is adapted to move the cannula yoke and the needle yoke from a storage state and to a first operational state where the needle and/or the cannula are in an insertion position. The drug delivery device may include a latching member to retain the cannula yoke in the first operational state. Further, the activation mechanism may additionally move the needle yoke to a second operational state where the needle is retracted, and may also urge the valve to the second position when the needle yoke is in the second operational state.

In some examples, the fluid flow connection may be constructed from a flexible tube.

In accordance with a second aspect, a needle insertion mechanism for a drug delivery device includes a cannula yoke, a cannula, a needle yoke, a needle, and a valve. The cannula yoke has a cannula coupling portion and is movable between a storage state and a first operational state. The cannula is coupled with the cannula coupling portion. The needle yoke has a needle coupling portion and is movable between a storage state, a first operational state, and a second operational state. The needle is coupled with the needle coupling portion. The valve is in fluid communication with the cannula and is movable between at least first and second positions. Upon the cannula yoke and the needle yoke moving from the storage state to the first operational state, the valve is configured to remain in the first position whereby fluid flow is restricted. At a later time, the valve is urged to the second position whereby fluid may flow through the cannula.

In accordance with a third aspect, a method of operating a drug delivery device is provided. The drug delivery device includes an activation mechanism, a container containing a medicament, and a needle insertion mechanism comprising a cannula yoke having a cannula coupled thereto, a needle yoke having a needle coupled thereto, and a valve in fluid communication with the cannula. The method includes moving the needle yoke from a storage state to a first operational state whereby the needle is in an inserted position and moving the cannula yoke from a storage state to a first operational state whereby the cannula is in an inserted position. The needle yoke is moved from the first operational state to a second operational state whereby the needle is in a retracted position. The valve is disposed in a first, closed position when the needle yoke is in the storage state and the first operational state. While the needle yoke is in the second operational state, the valve is moved to a second, open position that allows the medicament to flow from the container to the cannula.

In accordance with a fourth aspect, a drug delivery device includes a housing, a container, an activation mechanism, and a needle insertion mechanism. The container has an inner volume to contain a medicament which is urged out of the container by the activation mechanism. The needle insertion mechanism includes a needle and a cannula to deliver the medicament and is movable between a storage state and first, second, and third operational states. In the first operational state, the needle and cannula are in extended positions. In the second operational state, at least a portion of the needle insertion mechanism is disposed in a first position where medicament flow is restricted. In the third operational state, at least a portion of the needle insertion mechanism moves to a second position where flow of the medicament is permitted.

In accordance with a fifth aspect, a needle insertion mechanism for a drug delivery device includes a cannula yoke, a cannula, a needle yoke, a needle, and a valve. The cannula yoke has a cannula coupling portion and is movable between a storage position and a first operational position. The cannula is coupled with the cannula coupling portion. The needle yoke has a needle coupling portion and is movable between at least a storage position, a first operational position, and a second operational position. The needle is coupled with the needle coupling portion. The valve is in fluid communication with the cannula and includes a sealing sleeve and an urging member. The sealing sleeve is coupled with the needle and is movable between at least a first position and a second position. The urging member urges the sealing sleeve between the first and second positions. Upon the cannula yoke and the needle yoke moving from the storage position to the first operational position, the sealing sleeve is configured to remain in the first position whereby fluid flow is restricted. When the needle yoke is in the second operational position, the urging member urges the sealing sleeve to the second position whereby fluid may flow through the cannula.

In accordance with a sixth aspect, a drug delivery device includes a housing, a container, an activation mechanism, a needle insertion mechanism, and a valve. The container has an inner volume to contain a medicament which is urged out of the container by the activation mechanism. The needle insertion mechanism includes a needle and a cannula to deliver the medicament. The valve is in fluid communication with the cannula and includes a sealing sleeve and an urging member. The sealing sleeve is coupled with the needle and is movable between at least first and second positions. The urging member is configured to urge the sealing sleeve between the first and the second positions. Upon the needle insertion mechanism inserting the needle and the cannula, the sealing sleeve is configured to remain in the first position whereby fluid flow is restricted. At a later time, the urging member urges the sealing sleeve to the second position whereby fluid may flow through the cannula.

BRIEF DESCRIPTION OF THE DRAWINGS

The above needs are at least partially met through provision of the backflow prevention mechanism for a drug delivery device described in the following detailed description, particularly when studied in conjunction with the drawings, wherein.

The accompanying figures show embodiments according to the disclosure and are exemplary rather than limiting.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a drive system for a drug delivery device that includes a backflow prevention mechanism to prevent ingress of fluids (e.g., bodily fluids) into the drug delivery device. The drug delivery device may include a housing defining a shell and an inner volume, an activation mechanism, a container including a reservoir filled or adapted to be filled with a drug, a needle insertion mechanism, a fluid flow connection, and a backflow prevention mechanism in the form of a valve, each of which is at least partially disposed within the housing. The needle insertion mechanism is adapted to insert a needle and/or a cannula to deliver the medicament from the container via the fluid flow connection. The valve is in fluid communication with the fluid flow connection and needle insertion mechanism, and is movable between first and second positions.

The drug delivery devices described herein may have a delayed delivery, and as such, the needle and/or cannula may be inserted prior to drug delivery. Accordingly, upon insertion of the needle and/or the cannula, the valve remains in the first position whereby fluid flow is restricted. At a later time, the valve is urged to the second position whereby fluid may flow through the needle and/or cannula. The valve is a fluid path element disposed in the fluid path that selectively restricts and permits fluid flow through the needle and/or cannula. After the cannula is inserted, yet prior to drug delivery, the valve design allows the fluid flow path to remain sealed against the ingress of fluids (e.g., bodily fluids), thus reducing the likelihood of clogs or clots in the fluid path. Such a design is particularly advantageous for drug delivery devices having non-primed (air filled) fluid paths.

Figure 1:
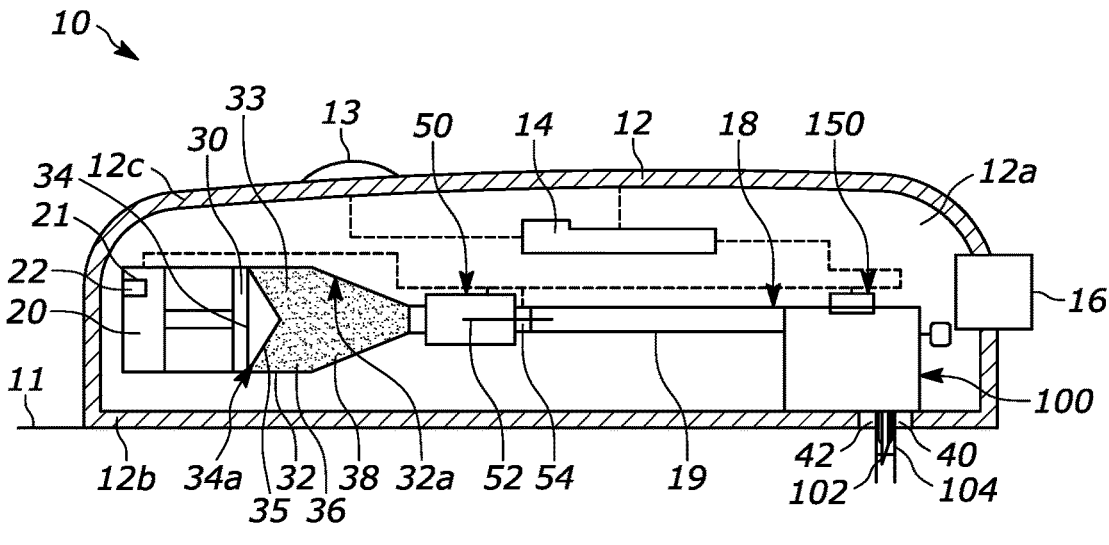
FIG. 1 illustrates a schematic representation of an example arrangement of a drug delivery device having a backflow prevention mechanism in accordance with various embodiments.

Referring to the Figures, a general drug delivery device 10 is provided that may include any number of aspects of the backflow prevention arrangement herein described. In some embodiments, including the one illustrated in FIG. 1, the drug delivery device 10 may be configured as a wearable drug delivery device, such as an on-body injector or an ambulatory infusion pump, that may be releasably coupled with a patient (e.g., to a patient's tissue 11 such as the patient's skin). In other embodiments, the drug delivery device 10 may be in the form of an autoinjector, a pen injector, or any other type of handheld device including hybrids thereof. The drug delivery device 10 may be operated to subcutaneously or transdermally deliver a drug to a patient. The drug delivery device 10 may be configured to automatically deliver a fixed or patient/operator-settable dose of a drug over a fixed or patient/operator-settable period of time. The drug delivery device 10 may be used for self-administration by the patient, or be used by a caregiver or a formally trained healthcare provider to administer an injection.

The drug delivery device 10 has a housing 12 that is releasably coupled with the patient's tissue 11 and that defines a shell and having an inner volume 12a, an activation mechanism 20, a container 30, a needle insertion mechanism 100, and a valve 150, each of which may be at least partially disposed within the housing 12. It is appreciated that the releasable coupling between the housing 12 and the patient's skin 11 can include any coupling or couplings that allow the drug delivery device 10 to be selectively secured to the patient, including the user holding the drug delivery device 10 against the injection site, a suction force, an adhesive, or other means of holding the drug delivery device 10 to the patient. Further, the drug delivery device may include a controller 14 and an actuator 16 (e.g., a depressible button) that is arranged on an exterior of the housing 12.

The container 30 (which, in some examples, may be referred to as a primary container) has a wall 32 that includes an interior surface 32a defining an interior volume 33 that accommodates a plunger 34. The plunger 34 is moveably disposed within the container 30 and has a first end 34a that includes an interior surface 35. The interior surface 32a of the container 30 and the interior surface 35 of the plunger 34 define a reservoir 36 that contains a drug or medicament 38.

The volume of the drug 38 contained in the reservoir 36 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 36 may be completely or partially filled with the drug or medicament 38. The drug or medicament 38 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The housing 12 may include a bottom wall 12b to contact or to be releasably coupled (e.g., adhered with an adhesive) with the patient's skin 11, and a top wall 12c including one or more visual feedback mechanisms 13 such as, for example a window, an opening, and/or an illumination system (not illustrated) for viewing the container 30 and the drug or medicament 38 contained therein. The one or more visual feedback mechanisms 13 may also be used to communicate information to the user about the operational state of the drug delivery device 10 and/or the condition of the drug or medicament 38. An opening 40 may be formed in the bottom wall 12b, and optionally a pierceable sterile barrier or septum 42 may extend across the opening 40 to seal the interior 12a of the housing 12 prior to use. In some embodiments, the pierceable sterile barrier 42 may be omitted, and instead a removable sealing member (not illustrated) may cover and seal the opening 40 prior to use. The exterior of the needle insertion mechanism 100 may be defined by a housing (not illustrated) that is separate from the drug delivery device housing 12.

A fluid flow connection 18 connects the container 30, and more specifically the reservoir 36, to the needle insertion mechanism 100. The actuator 16 is configured to initiate operation of the drug delivery device 10 by activating, via mechanical and/or electrical means (shown in dotted lines in FIG. 1), the activation mechanism 20, the needle insertion mechanism 100, the controller 14, and/or other mechanisms and/or electronics. In some examples, wireless communication may be employed to cause the drug delivery device 10 to be activated. In embodiments where the actuator 16 is a button that is depressed or otherwise physically moved by a user or patient, the actuator 16 may be configured to exert a motive force needed to activate the needle insertion mechanism 100, the fluid flow connection 18, the activation mechanism 20, the controller 14, and/or other mechanisms. In such embodiments, the actuator 16 may be physically connected to, either directly or indirectly via a mechanical linkage, the needle insertion mechanism 100, the activation mechanism 20, the fluid flow connection 18, and/or other mechanisms such that manually depressing or otherwise interacting with the actuator 16 supplies the motive force necessary to activate the needle insertion mechanism 100, the activation mechanism 20, the fluid flow connection 18, and/or other mechanisms.

The fluid flow connection 18 defines a sterile fluid flow path 19 between the container 30 and the needle insertion mechanism 100. The fluid flow connection 18 may be in the form of a flexible tube member. In some examples, a container access mechanism 50 is coupled with the fluid flow connection 18 and is configured to insert a container needle 52 through a seal member or septum 54 associated with and/or covering the container 30 to establish fluid communication between the container 30 and the sterile fluid flow path 19 in response to activation of the drug delivery device 10, for example, via the actuator 16. In the illustrated examples, relative movement between the container 30 and the container access mechanism 50 causes the container needle 52 to pierce the seal member or septum 54. In some examples, the container needle 52 may be staked to the container 30 such that the container needle 52 cannot move relative to the wall 32 of the container 30; whereas, in other examples, the container needle 52 may be moveable relative to the container 30 and may access the reservoir 36 of the container 30 by piercing through a septum or other sterile barrier covering an opening in the container 30 during operation or set up the drug delivery device 10. In some examples, the needle insertion mechanism 100 and the container 30 and/or other components such as the container access mechanism 50 may be integrated into a single unit, and thus the fluid flow connection 18 may not be included in the drug delivery device 10.

For example, in some embodiments, manually depressing or otherwise moving the actuator 16 may cause the fluid flow connection 18 and the container access mechanism 50 to move towards the container 30, or cause the container 30 to move towards the fluid flow connection 18 and the container access mechanism 50, and thereby cause the container needle 52 to penetrate through the seal member or septum 54, thereby establishing fluid communication between the reservoir 36 and the fluid flow path 19.

Additionally, or alternatively, the actuator 16 may operate as an input device that transmits an electrical, optical, and/or mechanical signal to the controller 14, which in turn may execute programmable instructions to control operation of the needle insertion mechanism 100, the activation mechanism 20, the fluid flow connection 18, and/or other mechanisms. In such embodiments, the controller 14 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 16 and which, in response to a control signal received from the controller 14, exerts the motive force needed to activate the needle insertion mechanism 100, the activation mechanism 20, the container access mechanism 50, and/or other mechanisms.

The activation mechanism 20 may include any number of components and/or sub-components to drive, urge, and/or exert a force on the plunger 34 to cause the drug or medicament 38 stored therein to be dispensed therefrom and optionally to also operate the needle insertion mechanism 100. In some examples, the activation mechanism 20 may use a drive fluid 22 in the form of compressed $CO_2$ gas or other compressed gas and/or a compressed liquid to drive, urge, and/or exert a drive force on the plunger 34. The drive fluid 22 may initially be stored within a pressure vessel or other container 21, and the activation mechanism 20 may be configured to release the compressed gas and/or liquid from the pressure vessel or other container 21 by opening a valve (not illustrated), which allows the compressed gas and/or liquid to flow into the container 30. In other examples, the activation mechanism 20 may be in the form of a hydro-pneumatic actuation system whereby a hydraulic and/or pneumatic force is exerted on the drive fluid 22 to move the plunger 34 through the container 30 to expel the drug 38 therefrom. In other examples, the activation mechanism 20 may include any number of resilient members (e.g., springs) that exert an urging force on the plunger 34. Examples of suitable activation mechanisms 20 are described in U.S. App. No. 62/543,058, filed on Aug. 9, 2017, the entire contents of which are incorporated by reference herein. Other examples of suitable activation mechanisms 20 are possible. In some examples, the activation mechanism 20 may supply the motive force to operate the needle insertion mechanism 100. In other examples, the motive force to operate the needle insertion mechanism 100 is instead supplied by a component or mechanism separate from the activation mechanism 20. In such examples the source of the motive force to operate the needle insertion mechanism 100 may be contained within the needle insertion mechanism 100 or external to it, depending on the specific embodiment.

With reference to FIGS. 2-6, the needle insertion mechanism 100 operates to insert a generally solid introducer needle 102 having a first end 102a and a second end 102b and a cannula 104 having a first end 104a and a second end 104b into the user. More specifically, the needle insertion mechanism 100 includes a needle yoke 110 and a cannula yoke 120. The needle yoke 110 defines a body that is operably coupled with the activation mechanism 20 and includes a needle coupling portion 112 to couple the needle 102 thereto. More specifically, in the illustrated example, the needle coupling portion 112 is in the form of a hole or an opening that accepts the second end 102*b* of the needle 102, which has a stopper or a plug 102*c* attached thereto. The needle 102 may be coupled with the needle yoke 110 via any number of approaches such as, for example, a friction fit coupling, an adhesive, a threaded coupling, and/or a fastener. Other examples are possible.

The cannula yoke 120 defines a body that is also operably coupled with the activation mechanism 20 and has a first end 120*a* and a second end 120*b*. The cannula yoke 120 includes a cannula yoke flow path 121 extending between the first and second ends 120*a*, 120*b*, a cannula coupling portion 122 to couple the cannula 104 thereto, a fluid flow connection coupling portion 124, and a valve coupling portion 126. More specifically, in the illustrated example, the cannula coupling portion 122 is in the form of a hole or an opening that defines a ledge 122*a* that accepts the second end 104*b* of the cannula 104. The cannula 104 may be coupled with the cannula yoke 120 via any number of approaches such as, for example, a friction fit coupling, an adhesive, a threaded coupling, via fasteners, etc.

The needle 102 may be constructed of material that is rigid or flexible. In examples where the needle 102 is rigid, the needle 102 may be made of a material that is more rigid and/or harder than the cannula 104. For example, the needle 102 may be made of metal and the cannula 104 may be made of plastic or another polymer. The relative flexibility of the cannula 104 may allow it to be disposed subcutaneously within the patient's tissue 11 for extended periods of time without causing pain or discomfort to the patient. In examples where the needle 102 is flexible, the needle 102 may be constructed from a superelastic material such as nitinol, a polymer, or another material that allows the needle 102 to follow a curved path without sustaining damage. In some examples, the needle 102 may function as a trocar for creating a pathway through the patient's tissue to facilitate insertion of the cannula 104. As will be discussed with reference to FIG. 5, immediately or shortly after the cannula 104 has been inserted, the needle 102 may be retracted back towards the housing 12 leaving the cannula 104 within the patient's tissue 11 for subcutaneous delivery of the drug 38.

The cannula 104 is in the form of a generally hollow member that permits fluid flow from the second end 104*b* to the first end 104*a*. The second end 104*b* of the cannula 104 defines an annular ledge 104*c* having a greater cross-sectional dimension (e.g., diameter) than the remainder of the cannula 104. In the illustrated examples, the annular ledge 104*c* couples to the ledge 122*a* of the cannula coupling portion 122.

The fluid flow connection coupling portion 124 is in the form of a hole or an opening that accepts a portion of the fluid flow connection 18. The fluid flow connection 18 may be coupled with the cannula yoke 120 via any number of approaches such as, for example, a friction fit coupling, an adhesive, a threaded coupling, and/or a fastener. Other examples are possible. The fluid flow connection 18 is positioned to define the opening of the cannula yoke flow path 121. As such, upon coupling the fluid flow connection 18 to the fluid flow connection coupling portion 124, the sterile fluid flow path 19 continues through the cannula yoke 120 and allows the drug or medicament 38 to exit at the second end 120*b* thereof.

The valve coupling portion 126 is in the form of a hole or an opening that accepts a portion of the valve 150. The valve 150 may be coupled with the cannula yoke 120 via any number of approaches such as, for example, a friction fit coupling, an adhesive, a threaded coupling, and/or a fastener. Other examples are possible. The valve coupling portion 126 is also positioned within the cannula yoke flow path 121 downstream of the fluid flow connection coupling portion 124, and as such, the valve 150 can selectively block the cannula yoke flow path 121 to restrict the drug or medicament 38 from flowing to the cannula 104.

More specifically, the valve 150 is moveably disposed within the valve coupling portion 126. The valve 150 includes a valve pin septum 152 and a valve pin 154. The valve pin septum 152 has a first throughbore 152*a* and a second throughbore 152*b* arranged approximately perpendicular to each other. As can be seen in the Figures, the first throughbore 152*a* is aligned with the cannula yoke flow path 121, and as such, the drug or medicament 38 can selectively flow through the first throughbore 152.

Generally, the valve pin 154 can selectively block flow through the first throughbore 152 by moving between first and second positions. More specifically, the valve pin 154 is movably disposed within the second throughbore 152*b* of the valve pin septum 152 and can selectively be disposed in a first position within the first throughbore 152*a* to restrict the drug or medicament 38 from flowing therethrough. The valve pin 154 is operably coupled with the activation mechanism 20, which urges or moves the valve pin 154 to a second position.

The valve pin septum 152 and/or the valve pin 154 may be constructed from any number of generally fluid-impermeable materials such as, for example pharmaceutically compatible silicone rubber, butyl rubber, butadiene rubber, neoprene, Viton, Buta-N, bromobutyl, chlorobutyl, Flurotec, and/or any other polymers and/or elastomeric materials, and can have additional coatings as lubricant or enhancements to barrier properties.

The needle insertion mechanism 100 may include any number of additional components such as, for example, a seal ring or septum 108 to guide movement of the needle 102 and/or to provide a sealing element to restrict the drug or medicament 38 (or any other fluid) from flowing to unintended areas of the drug delivery device 10.

Figure 3:
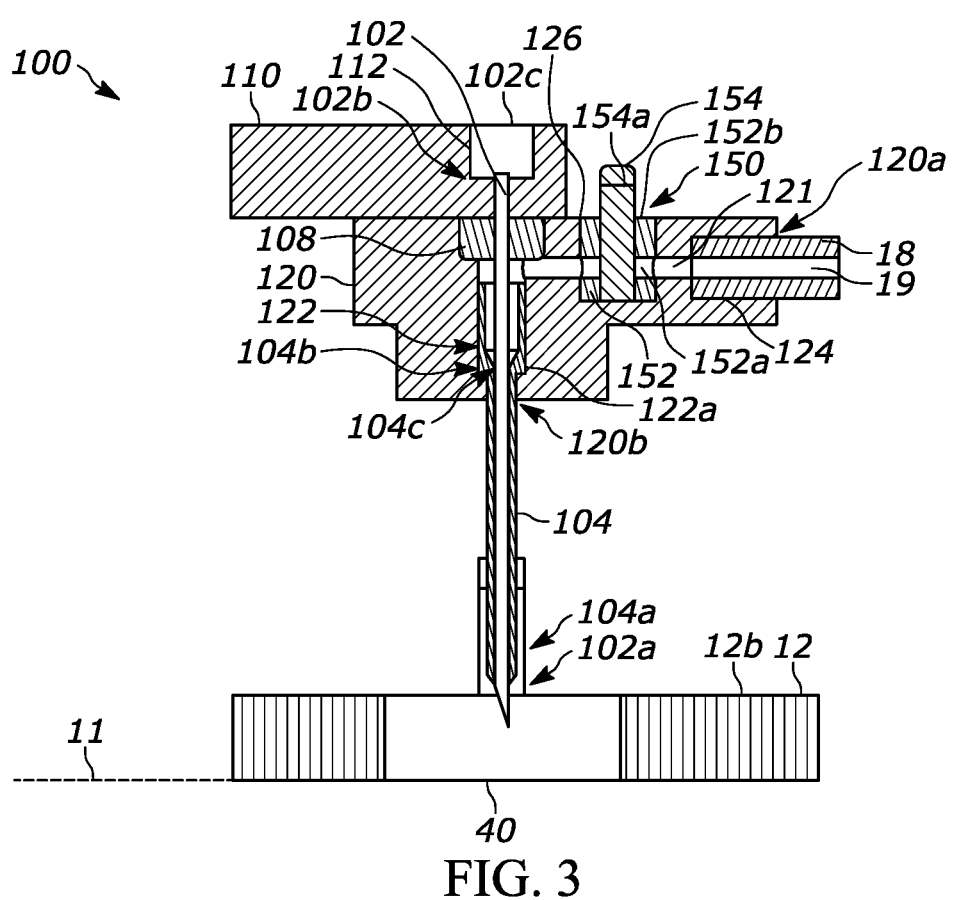
FIG. 3 illustrates the example needle insertion mechanism of FIG. 2 in a storage state in accordance with various embodiments.
Figure 4:
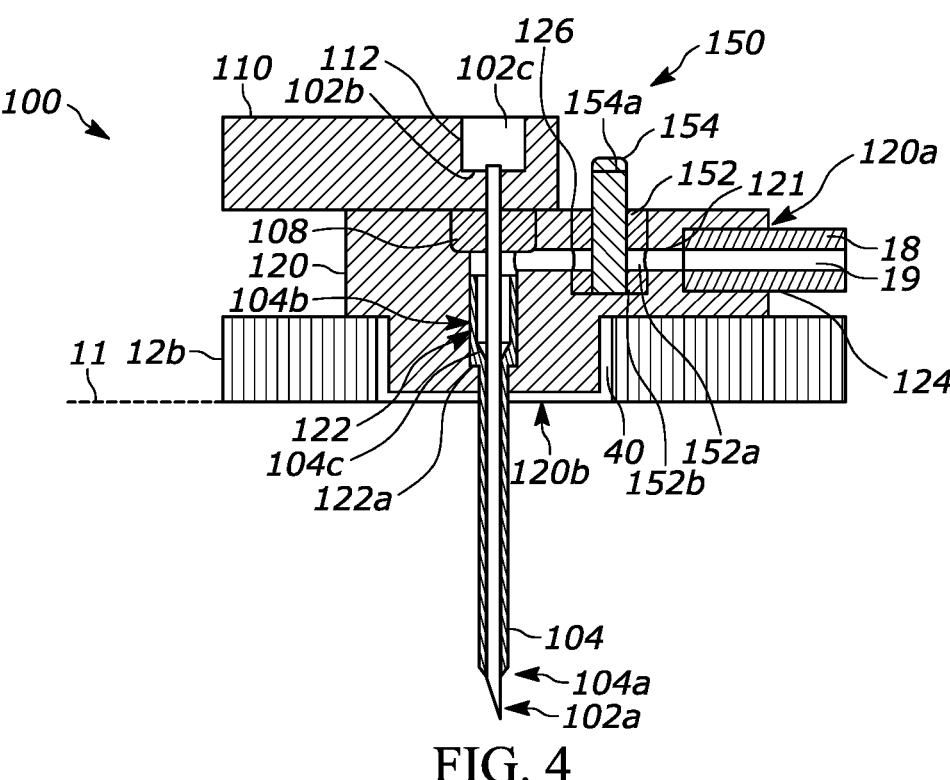
FIG. 4 illustrates the example needle insertion mechanism of FIGS. 2 and 3 in a first operational state (needle and cannula extended) in accordance with various embodiments.

With reference to FIG. 3, the needle yoke 110 and the cannula yoke 120 each have a storage state where the needle 102 and the cannula 104 is retracted within the housing 12. With reference to FIG. 4, after the bottom wall 12*b* of the housing 12 is attached to the patient's skin 11, upon engaging the activation mechanism 20 (e.g., via the actuator 16), the drug delivery device 10 may enable, connect, or open necessary connections to establish fluid communication between the container 30 and the fluid flow connection 18. Simultaneously or subsequently, the needle insertion mechanism 100 may be activated via the activation mechanism 20 to insert the needle 102 and the cannula 104 into the patient 11. More specifically, the needle yoke 110 and the cannula yoke 120 each move to a first operational state (e.g., a lowered state with respect to the illustrated orientation) which in turn causes the needle 102 and the cannula 104 to move outside of the housing 12. Put differently, the first ends 102*a*, 104*a* of the needle 102 and the cannula 104, respectively, are deployed from a retracted position to a deployed position through the opening 40 of the housing 12. In the present embodiment, this may include the needle insertion mechanism 100 inserting the needle 102 and the cannula 104 through the septum 42 and into the patient's skin 11 and subcutaneous tissue.

Figure 2:
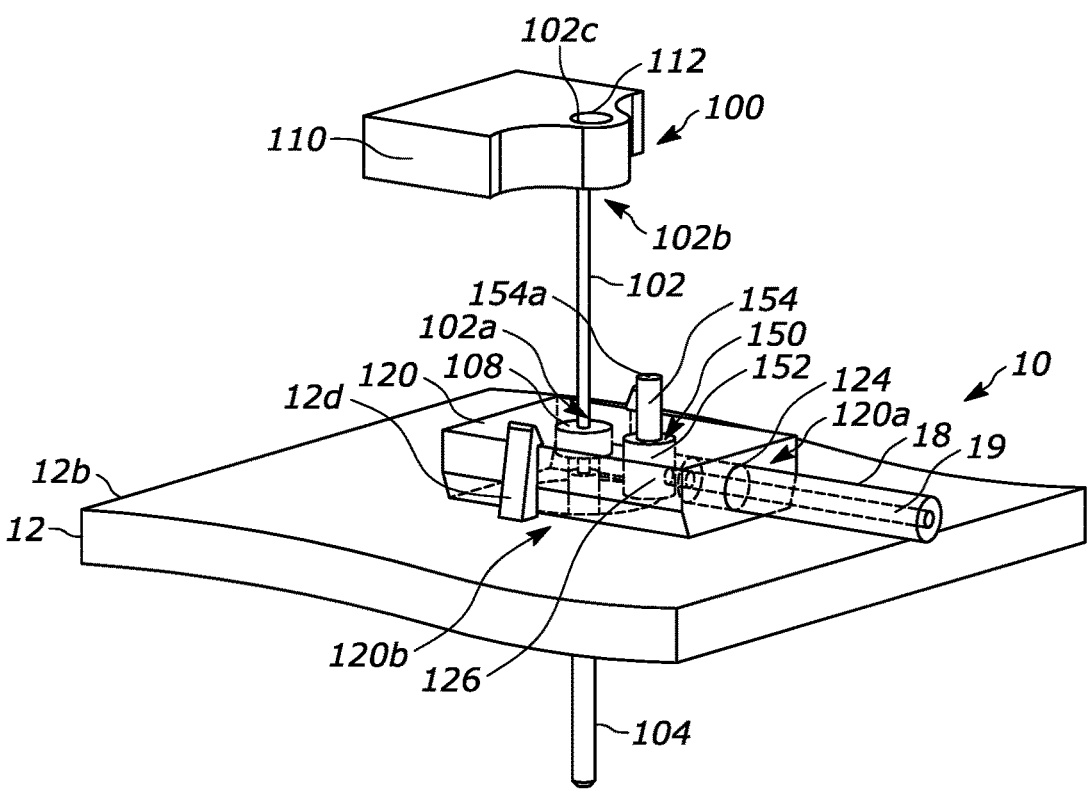
FIG. 2 illustrates an example needle insertion mechanism having a backflow prevention mechanism for the example drug delivery device of FIG. 1 in the form of an valve pin and an valve pin septum in accordance with various embodiments.

In the illustrated example, the second end 120*b* of the cannula yoke 120 is dimensioned to be inserted into the opening 40, and as illustrated in FIG. 2, a latching member 12*d* located on the bottom wall 12*b* of the housing 12 engages a portion of the cannula yoke 120 to retain and prevent the cannula yoke 120 from moving in an axial direction. Accordingly, the cannula 104 will remain in an extended position in the patient's subcutaneous tissue.

Figure 5:
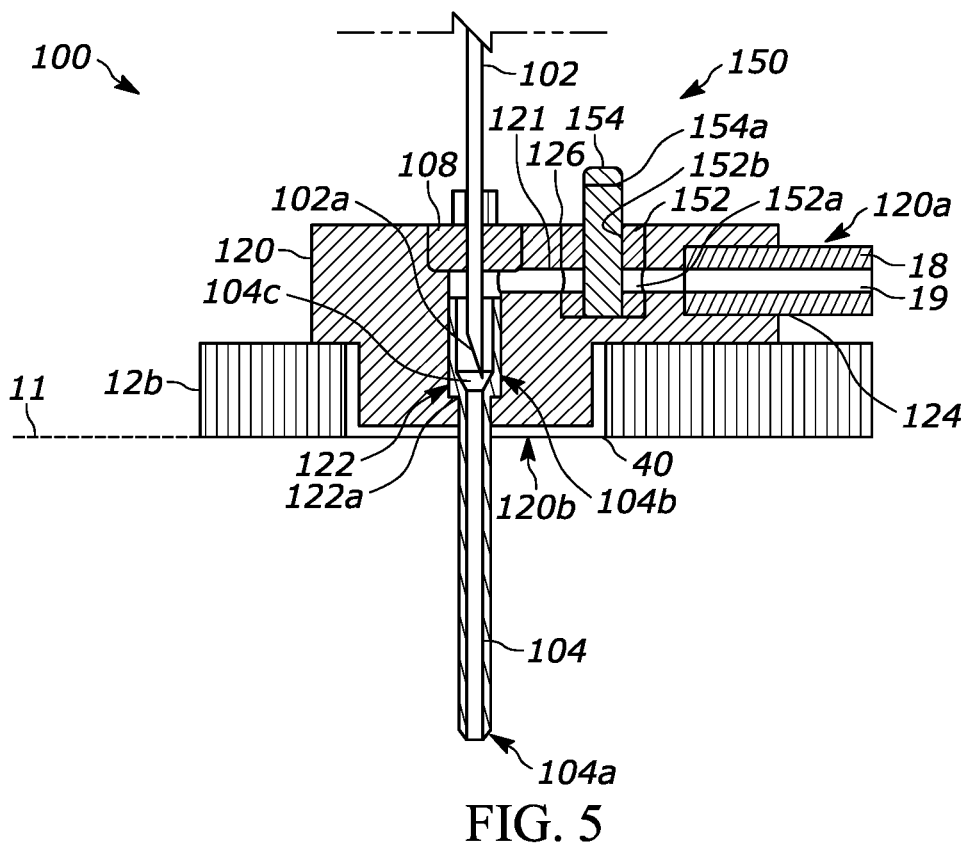
FIG. 5 illustrates the example needle insertion mechanism of FIGS. 2-4 in a second operational state (needle retracted, and valve closed) in accordance with various embodiments.

Turning to FIG. 5, immediately or shortly after the needle yoke 110 and the cannula yoke 120 are moved to the first operational state, the needle insertion mechanism 100 may automatically retract the needle yoke 110 (and thus the needle 102) to a second operational state, leaving the first end 104*a* of the distal open end of the cannula 104 inside the patient for subcutaneous delivery of the drug or medicament 38. As previously noted, the needle 102 may be solid and have a sharpened end for piercing the patient's skin 11, whereas the cannula 24 may be hollow and have a blunt end.

In some embodiments, the needle insertion mechanism 100 may include one or more springs (e.g., coil springs, torsion springs, etc., not illustrated) initially retained in an energized state, and which are released upon depression of the actuator 16 in order to insert the needle 102 and the cannula 104, into the patient. Furthermore, retraction of the needle 102 may be achieved by an automatic release of another spring after the needle 102 and the cannula 104 have been inserted into the patient. Other power sources for insertion and/or retraction are possible, including, for example, a portion of the activation mechanism 20, an electric motor, a hydraulic or pneumatic pump, or a canister that releases a pressurized gas or pressurized liquid to provide actuation energy. The power sources may also be paired with mechanical or electro-mechanical components for controlling movement of the needle 102 and/or the cannula 104, such as gears, scotch yoke arrangements, pivoting components, or sliding components.

When the drug delivery device 10 is in the configuration illustrated in FIG. 5, the valve pin 154 is in the first position to prevent the drug or medicament 38 from being urged through the cannula 104. Similarly, in this first position, the valve pin 154 blocks and prevents fluid from flowing back into the needle insertion mechanism 100 and/or the sterile fluid flow path 19, thereby reducing the likelihood of clot formation. The valve pin 154 remains in the first position until the drug or medicament 38 is administered, which may occur immediately thereafter, or after a user-selected or pre-determined delay (e.g., controlled by the actuator 16 and/or the controller 14).

Figure 6:
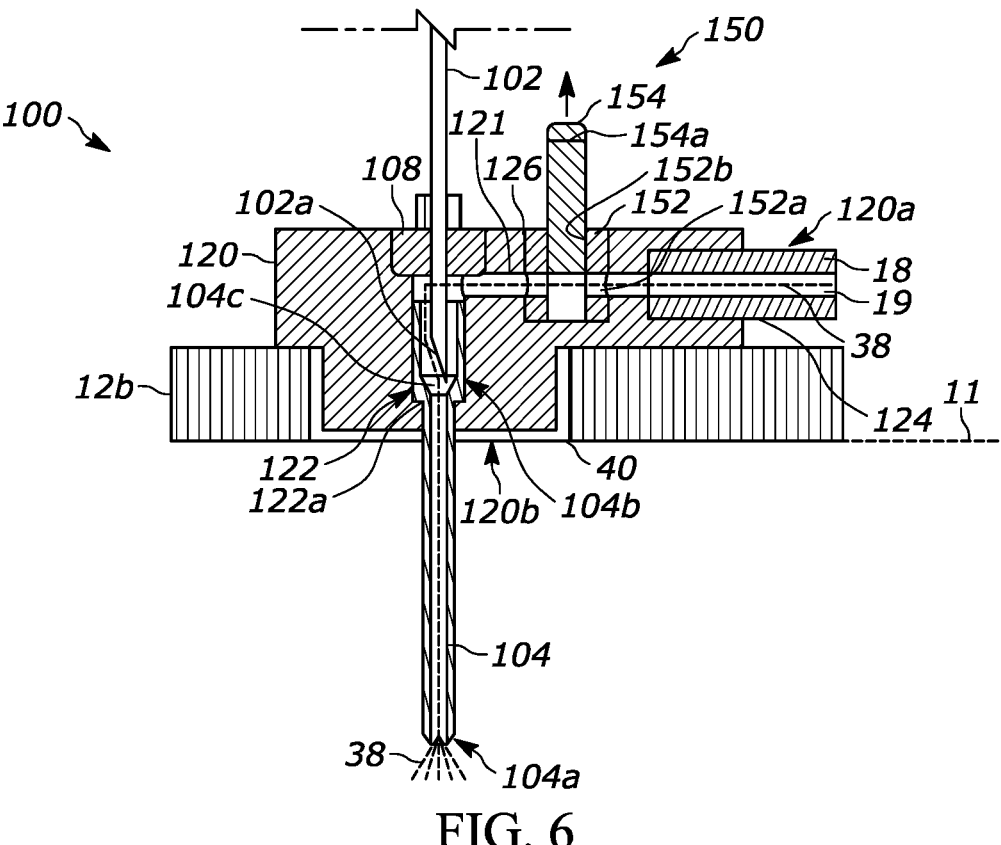
FIG. 6 illustrates the example needle insertion mechanism of FIGS. 2-5 in a third operational state (valve open) in accordance with various embodiments.

With reference to FIG. 6, at a later time, the needle insertion mechanism 100 moves to the third operational state (the needle yoke 110 is still in the second operational state), where the activation mechanism 20 exerts a force to translate or rotate the valve pin 154 relative to the valve pin septum 152 to move the valve pin 154 to the second position. More specifically, the activation mechanism 20 can include an urging mechanism (not illustrated) coupled to an electromechanical actuator (e.g., a shape-memory alloy, a muscle wire, a solenoid mechanism, a spring and fusible link mechanism, etc.) that moves the valve pin 154 to the second position. The electromechanical actuator may be coupled with the valve pin 154 at a coupling portion 154*a*, which, in the illustrated example, is in the form of a groove extending at least partially around an outer circumference of the valve pin 154. Other examples are possible. The muscle wire may be electrically coupled to a power source (e.g., a battery) that actuates and energizes the muscle wire to cause contraction, and thus urging or pulling, of the valve pin 154 to the second position. In some examples, the activation mechanism 20 may use an electromechanical polymer that may change shape or length in response to an electrical current or change in temperature. In any of these examples, the valve pin 154 itself may be constructed from an electromechanical polymer, a shape-memory alloy, and/or any other electromechanical actuator that is urged to the second position in response to an electrical current. Other mechanisms may be used to move the valve pin 154.

In some examples, the activation mechanism 20, by releasing or pushing on the drive fluid 22, may force the drug or medicament 38 stored in the container 30 through the sterile fluid flow path 19 of the fluid flow connection 18 and into the needle insertion mechanism 100 for subcutaneous delivery to the patient 11. More specifically, because the valve pin 154 is in the second position, the drug or medicament 38 is permitted to flow through the cannula yoke flow path 121 and out the second end of the cannula yoke 120, through the second end 104*b* of the cannula, and out the first end 104*a* thereof to deliver the drug or medicament 38. The activation mechanism 20 or any other component (e.g., a spring, a gear, etc.) may exert the force on the valve pin 154 to move it to the second position, thereby opening the fluid flow path 19. While the valve pin 154 is in the second position, it acts as a radial seal above the cannula yoke flow path 121 to prevent the drug or medicament 38 from flowing into unintended areas.

In the illustrated example, the valve pin 154 has a generally cylindrical geometry. However, in other examples, the valve pin 154 may have any desired shape and/or configuration. As previously noted, in some examples, the valve pin 154 may be translated through the second through-bore 152*b*, and in other examples, the valve pin 154 may be rotatably moved.

Figure 7:
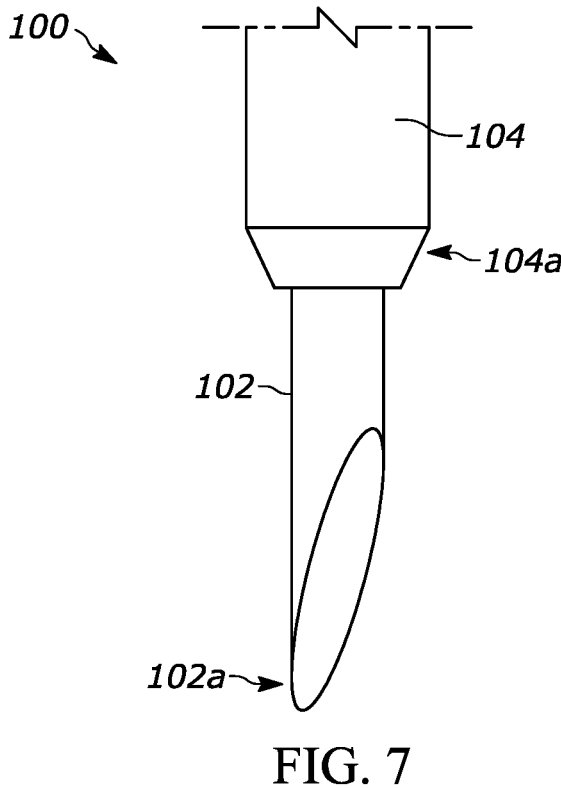
FIG. 7 illustrates a first example needle for use with the needle insertion mechanism of FIGS. 2-6 in accordance with various embodiments.
Figure 8:
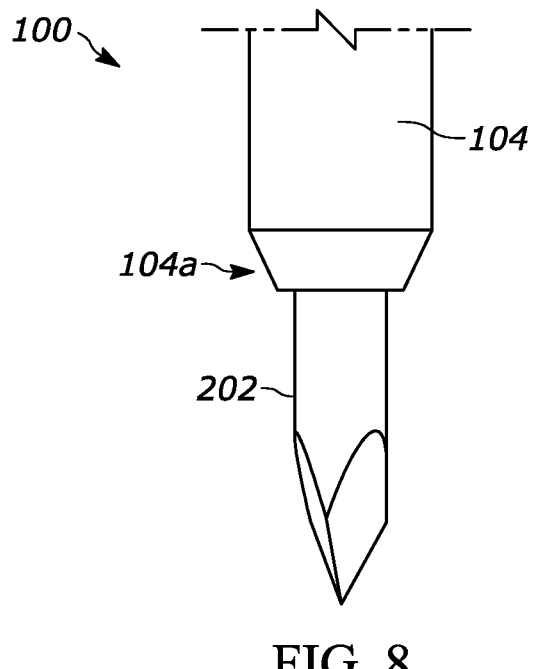
FIG. 8 illustrates a second example needle for use with the needle insertion mechanism of FIGS. 2-6 in accordance with various embodiments.

In various embodiments, different needle 102 geometries may be used. With reference to FIG. 7, a first needle 102 is provided in the form of a bevel tip needle 102. However, as illustrated in FIG. 8, a second needle 202 is provided in the form of a trocar style needle 202 having three symmetric bevels. Such a design can be made with a shorter tip geometry and can reduce needle protrusion from the cannula 104 during insertion to enable a shorter needle insertion mechanism 100. Other arrangements are possible.

So configured, the valve pin valve design allows the fluid path of the device to be selectively sealed against the ingress of bodily fluids, thus reducing the likelihood of clogs or clots in the fluid path. The valve pin valve design may be used in primed and/or non-primed (air filled) fluid paths because both may be susceptible to clot formation. However, the valve pin valve design may be particularly beneficial for on-body injectors having non-primed (air filled) fluid paths because air is easier to displace than liquids, meaning the bodily fluids have an increased likelihood of flowing in the reverse direction into the device. In both primed and non-primed systems, such backflow of bodily fluids can lead to clot formation, which in turn may reduce the size of the flow path which in turn may require increased forces to urge the drug or medicament through the fluid path to be administered. The valve described herein advantageously is positioned as close as possible to the inserted cannula 104 in order to minimize the volume of bodily fluid that may potentially enter the fluid path.

The needle insertion mechanisms 100 described herein may be constructed using any number of suitable alternative approaches. For example, FIGS. 9-13 illustrate an alternative example needle insertion mechanism 1100. It is appreciated that the needle insertion mechanism 1100 illustrated in FIGS. 9-13 may include similar features to the needle insertion mechanism 100 illustrated in FIGS. 1-8, and accordingly, elements illustrated in FIGS. 9-13 are designated by similar reference numbers indicated in the embodiment illustrated in FIGS. 1-8 increased by 1000. Accordingly, these features will not be described in substantial detail. Further, it is appreciated that any of the elements described with regards to the needle insertion mechanism 100 may be incorporated into the needle insertion mechanism 1100.

In this example, the needle insertion mechanism 1100 operates to insert a generally hollow needle 1102 having a closed first end 1102*a* and an open second end 1102*b* and a cannula 1104 having a first end 1104*a* and a second end 1104*b*. Generally, the needle insertion mechanism 1100 is movable between a storage state and a first operational state, between the first operational state and a second operational state, and between a second operational state and a third operational state.

More specifically, the needle insertion mechanism 1100 includes a needle yoke 1110 and a cannula yoke 1120. The needle yoke 1110 defines a body that, in some examples, is operably coupled with the activation mechanism 20 and includes a needle coupling portion 1112 to couple the needle 1102 thereto and further includes a fluid flow connection coupling portion 1114 to couple the fluid flow connection 1018 thereto. More specifically, in the illustrated example, the needle coupling portion 1112 is in the form of a hole or an opening that accepts the second end 1102*b* of the needle 1102. Similarly, in the illustrated example, the fluid flow connection coupling portion 1114 is in the form of an opening or a hole that receives a portion of the fluid flow connection 1018. As previously noted, example couplings between the needle 1102 and the fluid flow connection 1018 to the needle yoke 1110 may include friction fit connections, fasteners, snaps, threaded couplings, adhesives, and the like. Other examples are possible. When the fluid flow connection 1018 is coupled with the needle 1102 and the fluid flow connection coupling portion 1114 of the needle yoke 1110, the sterile fluid flow path 1019 continues through the needle 1102 and allows the drug or medicament 38 to exit at the first end 1102*a* thereof via the opening 1102*c*. In other examples, the needle yoke 1110 may have a separate source of drive force (e.g., a spring) separate from the activation mechanism 20.

As previously noted with reference to the cannula yoke 120, the cannula yoke 1120 defines a body that, in some examples, is also operably coupled with the activation mechanism 20 and has a first end 1120*a* and a second end 1120*b*. The cannula yoke 1120 includes a throughbore 1121 extending between the first and second ends 1120*a*, 1120*b* which defines a cannula coupling portion 1122 to couple the cannula 1104 thereto and a valve coupling portion 1124. More specifically, in the illustrated example, the cannula coupling portion 1122 is in the form of a hole or an opening that defines a ledge 1122*a* that accepts the second end 1104*b* of the cannula 1104. The cannula 1104 may be coupled with the cannula yoke 1120 via any number of approaches such as, for example, a friction fit coupling, an adhesive, a threaded coupling, fasteners, etc. Similarly, in the illustrated example, the valve coupling portion 1124 is in the form of a hole or an opening that defines a ledge 1124*a* that accepts a portion of the valve 1150, which will be discussed in further detail below. In other examples, the cannula yoke

1120 may have a separate source of drive force (e.g., a spring) separate from the activation mechanism 20.

Figure 13:
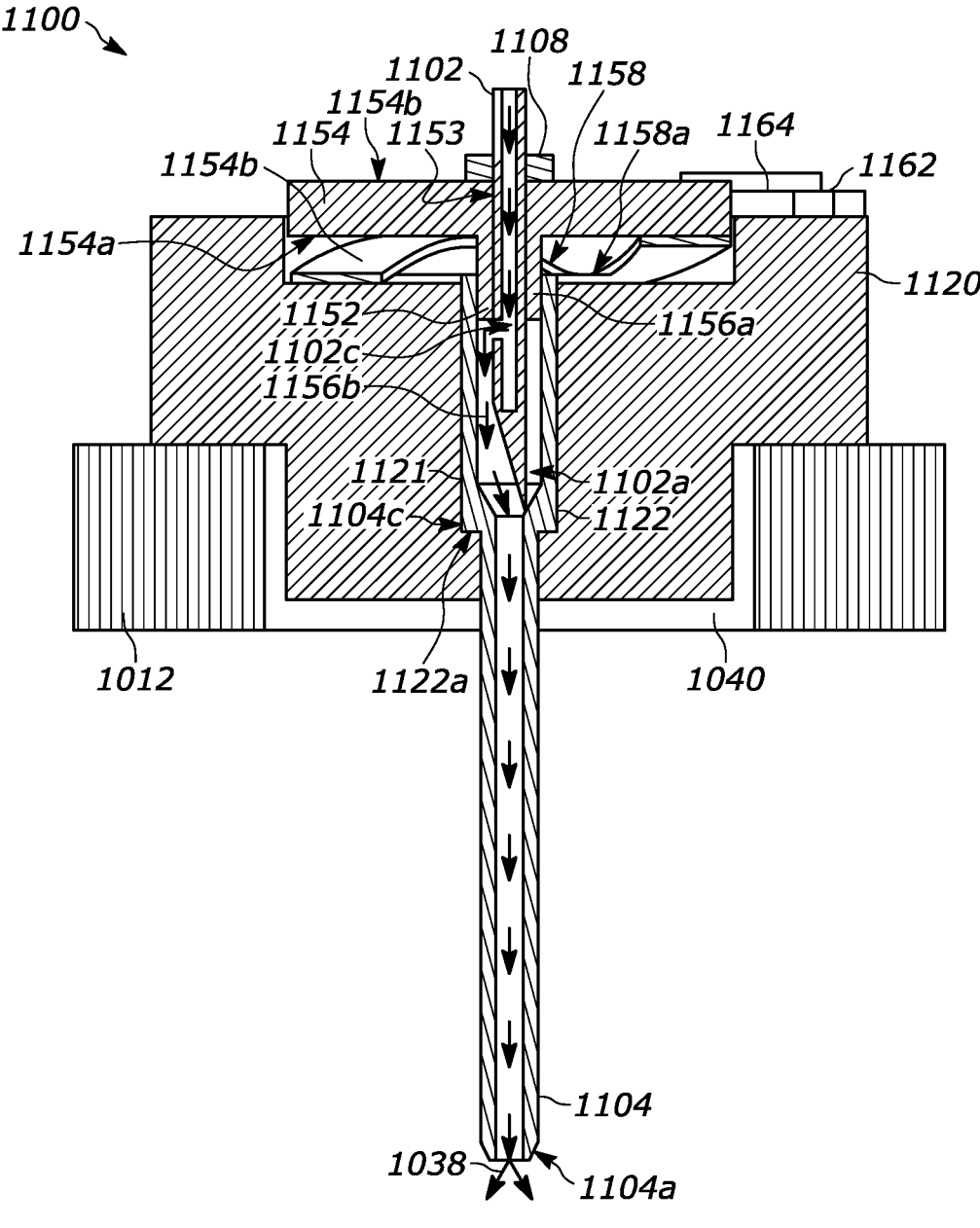
FIG. 13 illustrates the example needle insertion mechanism of FIGS. 9-12 in a third operational state (valve open) in accordance with various embodiments.

In the illustrated example, the needle 1102 is generally hollow to allow the drug or medicament 38 to flow from the second end 1102*b* to the first end 1102*a* thereof. More specifically, the second end 1102*b* of the needle 1102 is inserted into the fluid flow connection 1018, thereby allowing the drug or medicament 38 to flow through the needle 1102. In other examples (not illustrated), the fluid flow connection 1018 may be insertable into the needle 1102. As can be seen in FIG. 13, the first end 1102*a* of the needle 1102 further includes a side port or opening 1102*c* to allow the drug or medicament 38 to exit the needle 1102. As will be discussed with reference to FIG. 12, immediately or shortly after the cannula 1104 has been inserted, the needle 1102 may be retracted back towards the housing 1012 leaving the cannula 1104 within the patient's tissue 11 (FIG. 1) for subcutaneous delivery of the drug or medicament 38.

The cannula 1104 is in the form of a generally hollow member that permits fluid flow from the second end 1104*b* to the first end 1104*a*. The second end 1104*b* of the cannula 1104 defines an annular ledge 1104*c* having a greater cross-sectional dimension (e.g., diameter) than the remainder of the cannula 1104. In the illustrated examples, the annular ledge 1104*c* couples with and/or abuts against the ledge 1122*a* of the cannula coupling portion 1122.

The valve coupling portion 1124 is in the form of a hole or an opening that accepts a portion of the valve 1150. As will be discussed, in certain operational states of the needle insertion mechanism, a portion of the valve 1150 is positioned at or near the opening 1102*c* formed on the needle 1102, and as such, the valve 1150 can selectively block the opening 1102*c* to restrict the drug or medicament 38 from flowing to the cannula 1104.

The valve 1150 includes a sealing sleeve 1152, an urging member 1158, and a release tab 1162. The sealing sleeve 1152 is moveably disposed within the valve coupling portion 1124. The sealing sleeve 1152 has a body that includes a facing portion 1154 and an elongated portion 1156. A throughbore 1153 extends axially through the facing portion 1154 and the elongated portion 1156. The elongated portion 1156 further includes a closed portion 1156*a*. The end of the elongated portion 1156 defines a void 1156*b* that is formed between the sealing sleeve 1152 and the cannula 1104.

The facing portion 1154 has an outer dimension (e.g., a diameter) that is less than a corresponding dimension (e.g., a diameter) of the valve coupling portion 1124. Additionally, in the illustrated example, the throughbore 1153 has an inner dimension (e.g., a diameter) that is greater than or equal to an outer dimension (e.g., a diameter) of the needle 1102, and the elongated portion 1156 has an outer dimension (e.g., a diameter) that is less than or equal to an inner dimension (e.g., a diameter) of the second end of the cannula 1104*b*. So configured, the facing portion 1154 is dimensioned to be slidably inserted into the valve coupling portion 1124, the needle 1102 is dimensioned to be slidably inserted into the throughbore 1153, and the elongated portion 1156 is dimensioned to be slidably inserted into the second end 1104*b* of the cannula 1104. Accordingly, the sealing sleeve 1152 is movable relative to the cannula yoke 1120, the needle 1102, and/or the cannula 1104.

The urging member 1158 is in the form of a spring, and more specifically, a compressible wave spring 1158. The wave spring 1158 defines an opening 1158*a* that accommodates a portion of the elongated portion 1156 of the sealing sleeve 1152. In some examples, the opening 1158a may further accommodate a portion of the second end 1104b of the cannula 1104.

The release tab 1162 is a movable (e.g., pivotable) component that is coupled with the cannula yoke 1120. The release tab 1162 is operably coupled with the activation mechanism 20, which provides an urging or translating force to move the release tab 1162 from a first position to a second position. The release tab 1162 includes a pivot 1164 that pivotably couples to an opening formed on the cannula yoke 1120.

To assemble the valve 1150, the wave spring 1158 is disposed within the valve coupling portion 1124. The sealing sleeve 1152 is then also positioned within the valve coupling portion 1124, and as such, the wave spring 1158 abuts and/or is positioned adjacent to a first surface 1154a of the facing portion 1154. The wave spring 1158 is then compressed by urging the sealing sleeve 1152 further into the valve coupling portion 1124, and the release tab 1162 is then rotated to contact a second surface 1154b of the facing portion 1154. As a result, the sealing sleeve 1152 is retained in a first position.

The needle insertion mechanism 1100 may include any number of additional components such as, for example, a seal ring or septum 1108 to guide movement of the needle 1102 and/or to provide a sealing element to restrict the drug or medicament 38 (or any other fluid) from flowing to unintended areas of the drug delivery device 10.

Figure 10:
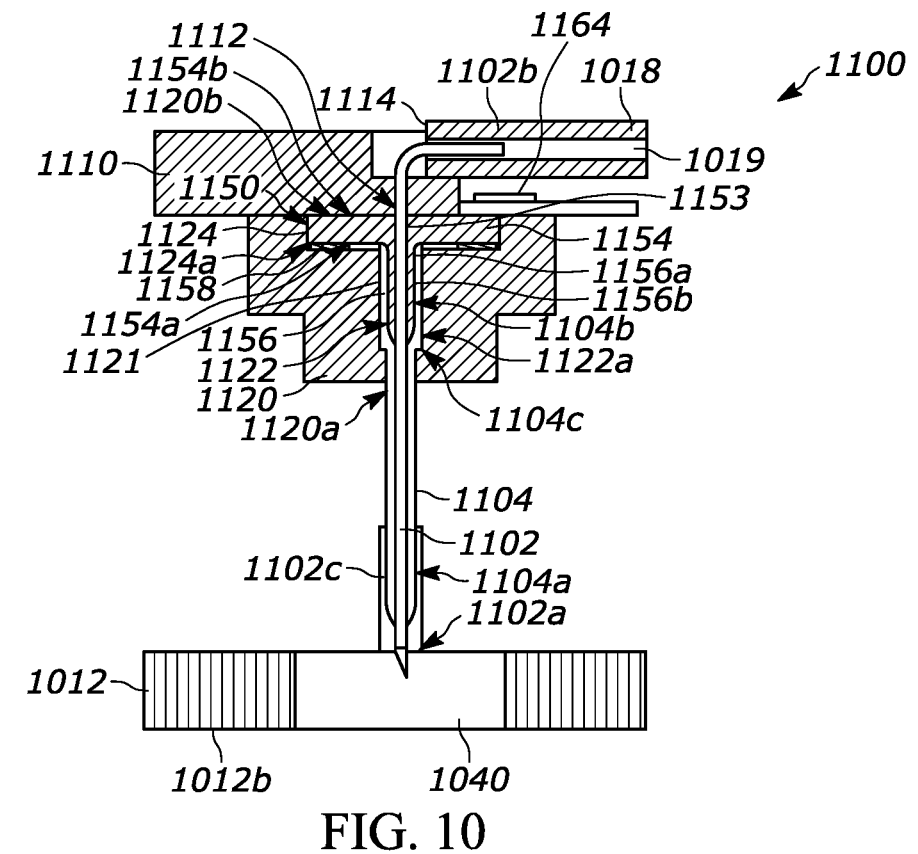
FIG. 10 illustrates the example needle insertion mechanism of FIG. 9 in a storage state in accordance with various embodiments.
Figures 11, 12:
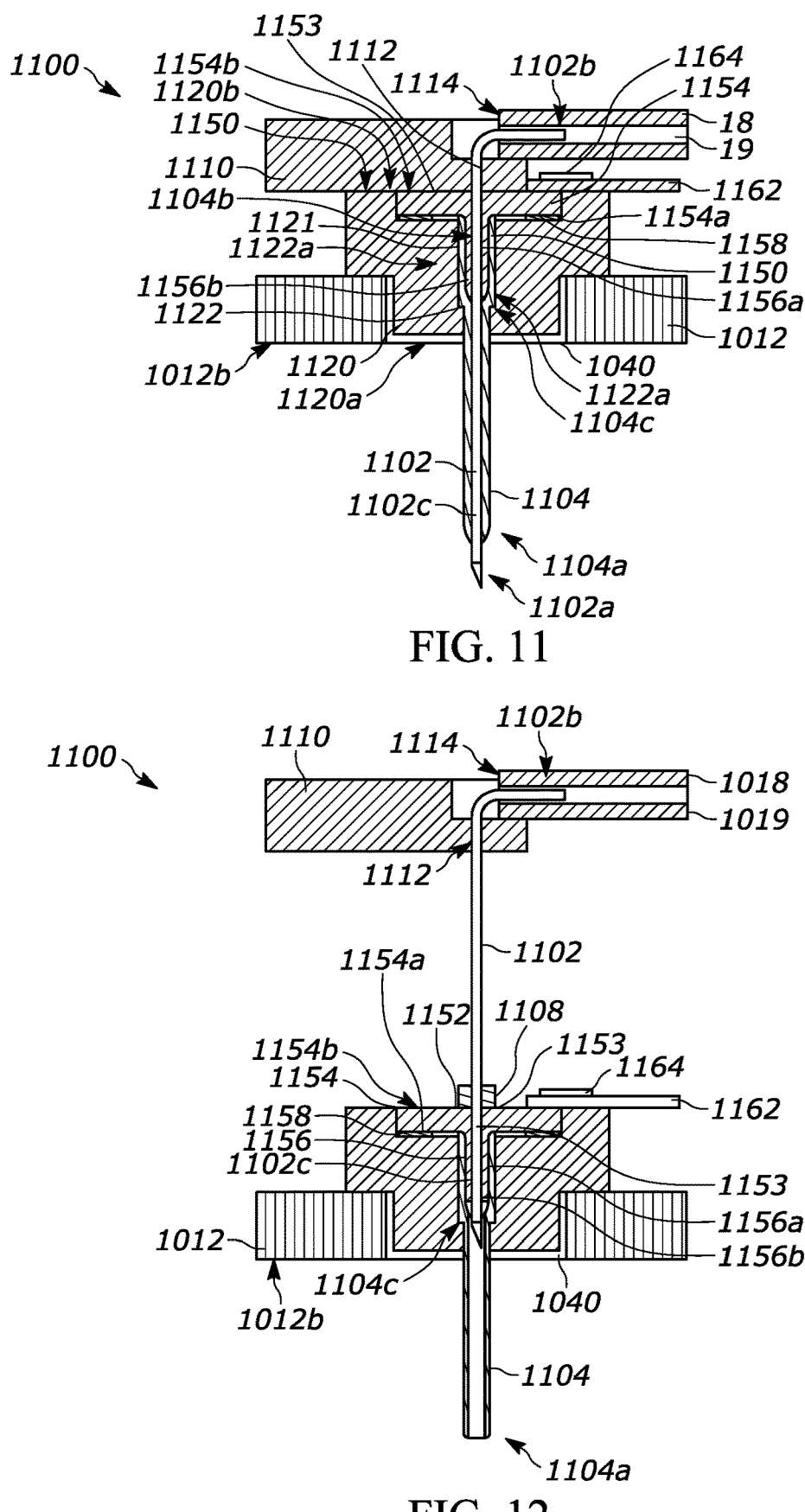
FIG. 11 illustrates the example needle insertion mechanism of FIGS. 9 and 10 in a first operational state (needle and cannula extended) in accordance with various embodiments.
FIG. 12 illustrates the example needle insertion mechanism of FIGS. 9-11 in a second operational state (needle retracted and valve closed) in accordance with various embodiments.

Generally speaking, the needle insertion mechanism 1100 is movable from a storage state to a first operational state, from the first operational state to a second operational state, and from the second operational state to a third operational state. With reference to FIG. 10, the needle insertion mechanism 1100 is in a storage state where needle yoke 1110 and the cannula yoke 1120 are in storage positions where the needle 1102 and the cannula 1104 are retracted within the housing 1012. With reference to FIG. 11, when the needle insertion mechanism 1100 is in the first operational state, the needle 1102 and the cannula 1104 are each in extended positions. More specifically, after the bottom wall 1012b of the housing 1012 is attached to the patient's skin 11, upon engaging the activation mechanism 20 (e.g., via the actuator 16), the drug delivery device 10 may enable, connect, or open necessary connections to establish fluid communication between the container 30 and the fluid flow connection 1018. Simultaneously or subsequently, the needle insertion mechanism 1100 may be activated via the activation mechanism 20 to insert the needle 1102 and the cannula 1104 into the patient's skin 11. Here, the needle yoke 1110 and the cannula yoke 1120 are positioned in the first operational position (e.g., a lowered position with respect to the illustrated orientation) which in turn causes the needle 1102 and the cannula 1104 to move to extended positions outside of the housing 1012. Put differently, the first ends 1102a and 1104a of the needle 1102 and the cannula 1104, respectively, are deployed from a retracted position to an extended position through the opening 1040 of the housing 1012. In the present embodiment, this may include the needle insertion mechanism 1100 inserting the needle 1102 and the cannula 1104 through the sterile barrier or septum 1042 (not illustrated) and into the patient's skin and subcutaneous tissue 11.

Figure 9:
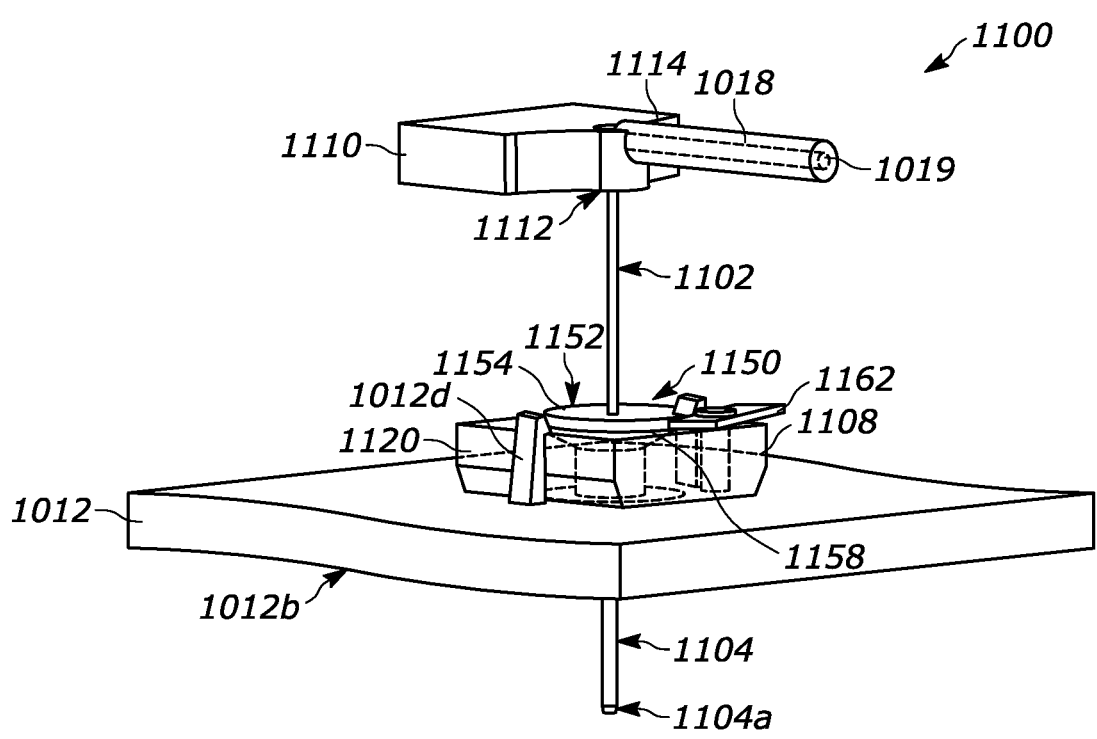
FIG. 9 illustrates an alternative example needle insertion mechanism having a backflow prevention mechanism for the example drug delivery device of FIG. 1 in the form of a sealing sleeve and an urging member in accordance with various embodiments.

In the illustrated example, the second end 1120b of the cannula yoke 1120 is dimensioned to be inserted into the opening 1040, and as illustrated in FIG. 9, latching members 1012d located on the bottom wall 1012b of the housing 1012 engages a portion of the cannula yoke 1120 to retain and prevent the cannula yoke 1120 from moving in an axial direction. Accordingly, the cannula 1104 will remain in an extended position in the subcutaneous tissue.

Turning to FIG. 12, immediately or shortly after the needle yoke 1110 and the cannula yoke 1120 are moved to respective first operational positions, the needle insertion mechanism 1100 may move to a second operational state (e.g., due to urging from the activation mechanism 20). The needle insertion mechanism 1100 may automatically retract the needle yoke 1110 to a second position (and thus the needle 1102), leaving the first end of the cannula 1104a inside the patient for subcutaneous delivery of the drug or medicament 38.

In some embodiments, the needle insertion mechanism 1100 may include one or more springs (e.g., coil springs, torsion springs, etc., not illustrated) initially retained in an energized state, and which are released upon depression of the actuator 16 in order to insert the needle 1102 and the cannula 1104, into the patient. Furthermore, retraction of the needle 1102 may be achieved by an automatic release of another spring after the needle 1102 and the cannula 1104 have been inserted into the patient. Other power sources for insertion and/or retraction are possible, including, for example, a portion of the activation mechanism 20, an electric motor, a hydraulic or pneumatic pump, or a canister that releases a pressurized gas or pressurized liquid to provide actuation energy. The power sources may also be paired with mechanical or electro-mechanical components for controlling movement of the needle 1102 and/or the cannula 1104, such as gears, scotch yoke arrangements, pivoting components, or sliding components.

When the needle insertion mechanism 1100 is in the second operational state illustrated in FIG. 12, the valve 1150, which is retained by the release tab 1162, is in the first, flow restricting position. More specifically, the opening 1102c formed on the needle 1102 is positioned adjacent to the closed portion 1156a of the elongated portion 1156 of the sealing sleeve 1152, and as such, the sealing sleeve 1152 blocks and/or seals the opening 1102c. Accordingly, the drug or medicament 38 is prevented from flowing out of the needle 1102. Similarly, in this first position, the sealing sleeve 1152 blocks and prevents fluid from flowing back into the needle insertion mechanism 1100 and/or the sterile fluid flow path 1019, thereby reducing the likelihood of clot formation. The dimensional tolerances between the exterior dimension of the needle 1102 and the interior dimension of the throughbore 1153 may be sufficiently small as to cause contact between the surfaces so that a liquid-tight seal is formed. The sealing sleeve 1152 remains in the first position until the drug or medicament 38 is administered, which may occur immediately thereafter, or after a user-selected or pre-determined delay (e.g., controlled by the actuator 16 and/or the controller 14).

With reference to FIG. 13, at a later time, the needle insertion mechanism 1100 moves to the third operational state where the sliding sleeve 1152 moves to a second position to permit fluid flow. In this third operational state, the needle yoke 1110 is still in the second operational position, and the activation mechanism 20 exerts a force to rotate or pivot the release tab 1162 about the pivot 1164, thus moving the release tab 1162 to the second position. More specifically, the activation mechanism 20 can include an urging mechanism (not illustrated) coupled to an electromechanical actuator (e.g., a shape-memory alloy, a muscle wire, a solenoid mechanism, a spring and fusible link mechanism, etc.) that moves the release tab 1162 to the second position. The electromechanical actuator may be coupled with the release tab 1162 via any number of suitable approaches. The muscle wire may be electrically coupled to a power source (e.g., a battery) that actuates and energizes the muscle wire to cause contraction, and thus urging or pulling, of the release tab 1162 to the second position. In some examples, the activation mechanism 20 may use an electromechanical polymer that may change shape or length in response to an electrical current or change in temperature. In any of these examples, the release tab 1162 itself may be constructed from an electromechanical polymer, a shape-memory alloy, and/or any other electromechanical actuator) that is urged to the second position in response to an electrical current. Other mechanisms may be used to move the release tab 1162.

As a result, the wave spring 1158 expands, and urges the sealing sleeve 1152 upwards to the second position by pressing against the first surface 1154*a* of the facing portion 1154. This movement causes the opening 1102*c* of the needle 1102 to become aligned with and disposed in the void 1156*c* formed between the sealing sleeve 1152 and the cannula 1104.

In some embodiments, the activation mechanism 20, by releasing or pushing on the drive fluid 22, may force the drug or medicament 38 stored in the container 30 through the sterile fluid flow path 1019 of the fluid flow connection 1018 and into the needle insertion mechanism 1100 for subcutaneous delivery into the patient's tissue 11. More specifically, because the sealing sleeve 1152 is in the second position, the drug or medicament 38 is permitted to flow out of the opening 1102*c* of the needle 1102, into the second end 1104*b* of the cannula 1104, and out the first end 1104*a* thereof to deliver the drug or medicament 38.

As previously noted, relative movement between the needle 1102 and the sealing sleeve 1152 selectively opens or closes the valve 1150. In some examples, to open the valve 1150, the sealing sleeve 1152 may remain stationary while the needle 1102 moves relative thereto to align the opening 1102*c* with the void 1156*b*.

Figure 14:
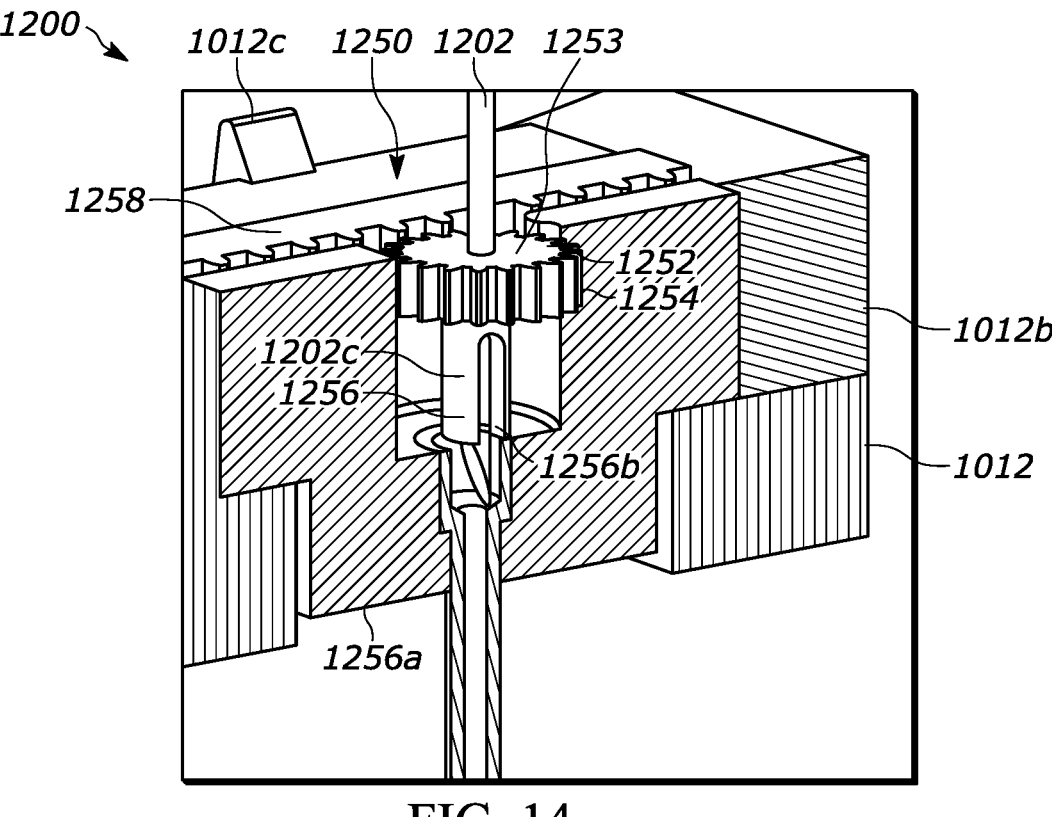
FIG. 14 illustrates a needle insertion mechanism having an alternative backflow prevention mechanism for use with the example drug delivery device of FIG. 1 in a closed position in accordance with various embodiments.
Figure 15:
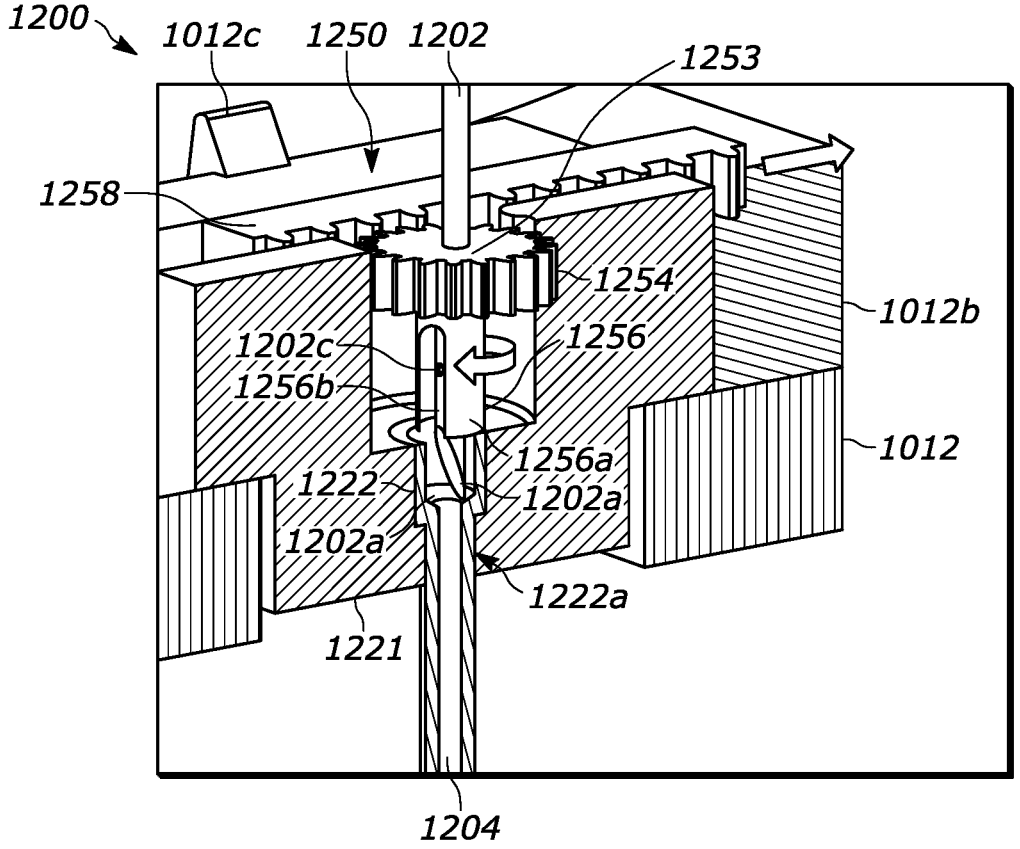
FIG. 15 illustrates the needle insertion mechanism of FIG. 14 whereby the alternative backflow prevention mechanism is in an open position in accordance with various embodiments.

In various embodiments, different valve arrangements may be used. With reference to FIGS. 14 and 15, an alternative needle insertion mechanism 1200 is described that includes similar features from the needle insertion mechanism 1100, and as such, these components include identical two-digit suffixes. For the sake of brevity, similar components will not be described in substantial detail. The valve 1250 includes a rotating sealing sleeve 1252 that has a gear portion 1254 which engages an urging member 1258 in the form of a drive gear 1258 which may be operably coupled with the activation mechanism 20 (or any other mechanism). In operation, the drive gear 1258 engages the gear portion 1254, causing the sealing sleeve 1252 to rotate about the needle 1202. Rotating the sealing sleeve 1252 causes an opening 1256*b* formed on the elongated portion 1256 to become aligned with the opening 1202*c* formed on the needle to allow the drug or medicament 38 to flow through the needle 1202, through the cannula 1204, and be delivered to the user.

So configured, the valve pin and sealing sleeve valve designs allow the fluid path of the drug delivery device to be selectively sealed against the ingress of bodily fluids, thus reducing the likelihood of clogs or clots in the fluid path. The valve designs may be used in primed and/or non-primed (air filled) fluid paths because both may be susceptible to clot formation. However, the valve designs may be particularly beneficial for on-body injectors having non-primed (air filled) fluid paths because air is easier to displace than liquids, meaning the bodily fluids have an increased likelihood of flowing in the reverse direction and into the drug delivery device. In both primed and non-primed systems, such backflow of bodily fluids can lead to clot formation, which in turn may reduce the size of the flow path which in turn may require increased forces to urge the drug or medicament through the flow connection to be administered. The valve described herein advantageously is positioned as close as possible to the first end of the inserted cannula in order to minimize the volume of bodily fluid that may potentially enter the fluid path.

Additionally, the needle insertion mechanisms 100, 1100, 1200 described herein separate actuation of the valve from the needle insertion process, thereby minimizing the overall height of the needle insertion mechanism by disposing the valve on a side of and/or within the cannula yoke as opposed to the top or other location of the needle insertion mechanism, which could result in needing a larger housing to accommodate the arrangement of components. It is desirable to provide a device having a small overall size, and as such, positioning the valve to a side of the needle insertion mechanism and/or within the cannula yoke aids in reducing the overall height of the drug delivery device.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen®

(epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb);

HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
   a housing defining a shell and an inner volume;
   a container at least partially disposed within the housing, the container having an inner volume to contain a medicament;
   an activation mechanism at least partially disposed within the housing, the activation mechanism adapted to exert a force to urge the medicament out the container;
   a needle insertion mechanism at least partially disposed within the housing, the needle insertion mechanism adapted to insert a needle and/or a cannula to deliver the medicament;
   a fluid flow connection coupled with the container and the needle insertion mechanism, the fluid flow connection adapted to allow the medicament to flow from the container to the needle insertion mechanism; and
   a valve in fluid communication with the fluid flow connection and the needle insertion mechanism, the valve being movable between at least a first position and a second position, wherein the valve comprises a valve pin septum including a first throughbore and a second throughbore and a valve pin movably disposed within the second throughbore, where the valve pin is positioned within the first throughbore when in the first position to restrict medicament flow and is positioned to permit medicament flow through the first throughbore when in the second position;
   wherein upon the needle insertion mechanism inserting the needle and/or the cannula, the valve is configured to remain in the first position whereby fluid flow from the container to the needle or cannula is restricted for a predetermined delay period, and at a later time, the valve is urged to the second position whereby fluid may flow through the needle or cannula.

2. The drug delivery device of claim 1, wherein the activation mechanism is operably coupled with the valve pin to move the valve pin between the first and second positions.

3. The drug delivery device of claim 1, wherein the needle insertion mechanism further comprises:
   a needle yoke operably coupled with the activation mechanism, the needle yoke including a needle coupling portion to receive a portion of the needle;
   a cannula yoke operably coupled with the activation mechanism, the cannula yoke including a cannula coupling portion to receive a portion of the cannula, a fluid flow connection coupling portion to receive a portion of the fluid flow connection, and a valve coupling portion to receive a portion of the valve.

4. The drug delivery device of claim 3, wherein the activation mechanism is adapted to move the cannula yoke and the needle yoke from a storage state to a first operational state where the needle and/or the cannula are in an insertion position.

5. The drug delivery device of claim 3, wherein the activation mechanism is further adapted to move the needle yoke to a second operational state where the needle is retracted, wherein the activation mechanism is further optionally adapted to urge the valve to the second position when the needle yoke is in the second operational state.

\* \* \* \* \*